United States Patent
Sonobe et al.

(10) Patent No.: US 9,953,115 B2
(45) Date of Patent: Apr. 24, 2018

(54) METHOD FOR SPECIFYING STRETCH FLANGE LIMIT STRAIN AND METHOD FOR DETERMINING FEASIBILITY OF PRESS FORMING

(71) Applicant: JFE STEEL CORPORATION, Tokyo (JP)

(72) Inventors: Osamu Sonobe, Tokyo (JP); Akinobu Ishiwatari, Tokyo (JP); Masaki Urabe, Tokyo (JP); Hirotaka Kano, Tokyo (JP); Jiro Hiramoto, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 421 days.

(21) Appl. No.: 14/436,236

(22) PCT Filed: Oct. 10, 2013

(86) PCT No.: PCT/JP2013/077595
§ 371 (c)(1),
(2) Date: Apr. 16, 2015

(87) PCT Pub. No.: WO2014/077060
PCT Pub. Date: May 22, 2014

(65) Prior Publication Data
US 2015/0294043 A1 Oct. 15, 2015

(30) Foreign Application Priority Data

Nov. 19, 2012 (JP) .................. 2012-253474
Jul. 23, 2013 (JP) .................. 2013-152230

(51) Int. Cl.
*G06F 17/50* (2006.01)
*G06F 17/10* (2006.01)
(Continued)

(52) U.S. Cl.
CPC ......... *G06F 17/5009* (2013.01); *B21D 22/02* (2013.01); *G01L 5/00* (2013.01);
(Continued)

(58) Field of Classification Search
CPC ..... G06F 17/5009; G06F 17/10; B21D 22/02; B21D 19/00; B21D 53/88; G01L 5/00;
(Continued)

(56) References Cited

FOREIGN PATENT DOCUMENTS

JP 2006-155254 A 6/2006
JP 2009-172609 A 8/2009
(Continued)

OTHER PUBLICATIONS

English machine translation of JP 2010069533, Takashi Matsuno, Apr. 2010.*
Jun. 13, 2016 Extended Search Report issued in European Patent Application No. 13855369.8.
Apr. 11, 2017 Office Action issued with Korean Patent Application No. 10-2015-7012761.
(Continued)

*Primary Examiner* — Manuel L Barbee
(74) *Attorney, Agent, or Firm* — Oliff PLC

(57) ABSTRACT

A method for manufacturing a press formed part, the method including specifying stretch flange limit strain in a metal sheet by using strain gradient in a radial direction and strain gradient in a sheet thickness direction. The strain gradient in the radial direction being directed from an end portion of the metal sheet at a time a press load is applied. The strain gradient in the sheet thickness direction being a direction of the metal sheet that intersects a loading direction. Additionally, the stretch flange limit strain satisfies the formula $\epsilon_{\theta lim} = A[a \cdot \Delta\epsilon_\theta/\Delta r + b \cdot \Delta\epsilon_\theta/\Delta t] + c$, where $\epsilon_{\theta lim}$ represents the stretch flange limit strain in a tangential direction of the sheet edge, $\Delta\epsilon_\theta/\Delta r$ represents the strain gradient in the radial direction, $\Delta\epsilon_\theta/\Delta t$ represents the strain gradient in the sheet thickness direction, A, a, and b represent influence coefficients, and c represents the limit strain at a time the strain gradient is zero.

4 Claims, 11 Drawing Sheets

(a)

(b)

(51) Int. Cl.
*G01L 5/00* (2006.01)
*B21D 22/02* (2006.01)
*G01N 3/28* (2006.01)
*G01M 99/00* (2011.01)
*B21D 19/00* (2006.01)
*B21D 53/88* (2006.01)

(52) U.S. Cl.
CPC ............ *G01M 99/007* (2013.01); *G01N 3/28* (2013.01); *G06F 17/10* (2013.01); *B21D 19/00* (2013.01); *B21D 53/88* (2013.01); *G01N 2203/0075* (2013.01); *G01N 2203/027* (2013.01); *G01N 2203/0254* (2013.01)

(58) Field of Classification Search
CPC .................. G01M 99/007; G01N 3/28; G01N 2203/0075; G01N 2203/0254; G01N 2203/027
See application file for complete search history.

(56) References Cited

FOREIGN PATENT DOCUMENTS

| | | | |
|---|---|---|---|
| JP | 2010-069533 A | | 4/2010 |
| JP | 2010069533 A | * | 4/2010 |
| JP | 2011-043452 A | | 3/2011 |
| JP | 2011-083813 A | | 4/2011 |
| JP | 2011-140046 A | | 7/2011 |
| JP | 4935713 B2 | | 5/2012 |

OTHER PUBLICATIONS

Nov. 26, 2013 International Search Report issued in International Patent Application No. PCT/JP2013/077595.

Dec. 6, 2016 Office Action issued in Chinese Patent Application No. 201380060152.4.

* cited by examiner (a)

(b)

(a)

(b)

(a)    (b)

METHOD FOR SPECIFYING STRETCH FLANGE LIMIT STRAIN AND METHOD FOR DETERMINING FEASIBILITY OF PRESS FORMING

FIELD

The present invention relates to a method for specifying stretch flange limit strain generated at a sheared edge of a press formed part, and a method for determining feasibility of press forming by using the method for specifying stretch flange limit strain.

BACKGROUND

Press formed parts (for example, press formed parts for automobiles) are formed in mass-production by a press forming process using a die. In most cases, such a press forming process is accompanied by stretch flange forming. In the stretch flange forming, a sheet edge may reach a fracture limit and a crack may be caused in the process of press forming depending on forming specifications (such as shape of a forming product and a shape of a press die). Therefore, selecting an appropriate forming specification is important. In order to select the appropriate forming specification, it is necessary to determine whether the sheet edge reaches the fracture limit at the time of actual forming in accordance with the forming specification. However, a deformation mode the sheet edge by executing the stretch flange forming is varied by a portion and cannot be uniformly defined. Therefore, a unified index applicable to any kind of deformation mode is needed to determine feasibility of forming.

As an exemplary method of obtaining such a unified index, there are methods disclosed in Patent Literatures 1 and 2, for example, in which material testing and analysis finite element analysis (FEM analysis) by Finite Element Method (FEM) are combined. The method disclosed in Patent Literature 1 is, for example, a hole expansion test executed under various kinds of industrial tool conditions and hole diameter conditions (refer to FIG. 19). FIG. 19(a) is a diagram illustrating a hole expansion test with a conical punch and FIG. 19(b) is a diagram illustrating a hole expansion test with a flat bottomed cylindrical punch. By executing the above hole expansion tests, a fracture limit is examined (material test), and fracture limit strain (stretch flange limit strain) at a hole edge and strain gradient in a radial direction from the hole edge are calculated by the FEM analysis. Based on a relation between the calculated stretch flange limit strain and the strain gradient in the radial direction, a stretch flange limit strain curve is obtained and applied as the index. An example of the stretch flange limit strain curve obtained by this method is illustrated in FIG. 20.

Further, according to the method disclosed in Patent Literature 2, side bend tests are executed on test pieces formed like an arc-shaped sheet edge having different curvature to obtain sheet edge strain at a fracture limit, a stretch flange forming limit of a material is obtained based on a relational formula in which the obtained sheet edge strain at the fracture limit and strain gradients in both a radial direction and a tangential direction of the arc shaped sheet edge are considered. Then, the obtained stretch flange forming limit of the material is compared with an FEM forming analysis result on an actual component.

CITATION LIST

Patent Literature 1: Japanese Patent No. 4935713
Patent Literature 2: Japanese Patent Application Laid-open No. 2011-140046

SUMMARY

Technical Problem

In the case of forming a so-called thick sheet used for such as a suspension part and having a relatively large sheet thickness and high strength, a large difference due to forming conditions is caused in strain distribution in a sheet thickness direction. Such an influence cannot be ignored in the case where the thick sheet has the sheet thickness of 2.0 mm or more. However, according to the technique disclosed in Patent Literature 1, no consideration is given to the influence of the strain distribution in the sheet thickness direction. Therefore, in the case where the sheet thickness is large, the relation between the stretch flange limit strain and the strain gradient in the radial direction is widely varied and may be insufficient to be the index of the stretch flange limit strain.

The present invention has been made to solve the above problem, and an object thereof is to provide a method for specifying limit strain of the stretch flange (stretch flange limit strain) applicable at the time of press forming a metal sheet having large sheet thickness, and a method for determining feasibility of press forming by using the method for specifying the stretch flange limit strain.

Solution to Problem

A method for specifying stretch flange limit strain according to the present invention includes specifying stretch flange limit strain so as to satisfy a relation in a following formula by using: strain gradient in an inward direction directed from an end portion of a metal sheet at a time a press load is applied; and strain gradient in a sheet thickness direction of the metal sheet intersecting the loading direction.

$$\epsilon_{\theta lim} = A[a \cdot \Delta\epsilon_\theta/\Delta r + b \cdot \Delta\epsilon_\theta/\Delta t] + c$$

where $\epsilon_{\theta lim}$ represents the stretch flange limit strain (tangential direction of a sheet edge),
$\Delta\epsilon_\theta/\Delta r$ represents the strain gradient in the inward direction,
$\Delta\epsilon_\theta/\Delta t$ represents the strain gradient in the sheet thickness direction,
A, a, and b represent influence coefficients, and
c represents the limit strain at a time the strain gradient is zero.

A method for specifying stretch flange limit strain according to the present invention includes specifying stretch flange limit strain so as to satisfy a relation in a following formula by using strain gradient in a sheet thickness direction of a metal sheet intersecting a loading direction at a time a press load is applied.

$$\epsilon_{\theta lim} = A[b \cdot \Delta\epsilon_\theta/\Delta t] + c$$

where $\epsilon_{\theta lim}$ represents the stretch flange limit strain (tangential direction of the sheet edge),
$\Delta\epsilon_\theta/\Delta t$ represents the strain gradient in the sheet thickness direction,
A and b represent influence coefficients, and
c represents the limit strain at a time the strain gradient is zero.

A method for determining feasibility of press forming of a metal sheet according to the present invention includes the steps of: acquiring stretch flange limit strain at a sheared edge by executing a hole expansion test using a metal sheet while changing a diameter of an initial hole and a shape of a hole expanding punch; obtaining strain gradient in a radial direction of the initial hole near the sheared edge after the hole expansion test; obtaining strain gradient in a sheet thickness direction near the sheared edge after the hole expansion test; and determining feasibility of press forming which causes stretch flange strain, by using an empirical formula representing a relation between stretch flange limit strain $\epsilon_{\theta lim}$ and a value $[a \cdot \Delta\epsilon_\theta/\Delta r + b \cdot \Delta\epsilon_\theta/\Delta t]$ obtained by adding the strain gradient in the radial direction with the strain gradient in the sheet thickness direction, wherein the empirical formula is obtained by using: the stretch flange limit strain acquired in the step of acquiring the stretch flange limit strain; the strain gradient in the radial direction obtained in the step of obtaining the strain gradient in the radial direction; and the strain gradient in the sheet thickness direction obtained in the step of obtaining the strain gradient in the sheet thickness direction.

A method for determining feasibility of press forming of a metal sheet according to the present invention includes the steps of: acquiring stretch flange limit strain at a sheared edge by executing a hole expansion test using a metal sheet while changing a diameter of an initial hole and a shape of a hole expanding punch; obtaining strain gradient in a sheet thickness direction near the sheared edge after the hole expansion test; and determining feasibility of press forming which causes stretch flange strain, by using an empirical formula representing a relation between stretch flange limit strain $\epsilon_{\theta lim}$ and the strain gradient in the sheet thickness direction $[b \cdot \Delta\epsilon_\theta/\Delta t]$, wherein the empirical formula is obtained by using: the stretch flange limit strain acquired in the step of acquiring the stretch flange limit strain; and the strain gradient in the sheet thickness direction obtained in the step of obtaining the strain gradient in the sheet thickness direction.

Advantageous Effects of Invention

According to the present invention, stretch flange limit strain at the time of press forming a metal sheet having large sheet thickness can be predicted with high accuracy by obtaining a relation between the stretch flange limit strain and strain gradient (strain gradient in a radial direction (inward direction) and strain gradient in a sheet thickness direction, or the strain gradient in the sheet thickness direction).

BRIEF DESCRIPTION OF DRAWINGS

FIG. 19 is an explanatory diagram for describing the hole expansion test and the like.

DESCRIPTION OF EMBODIMENTS

First Embodiment

In the method of specifying stretch flange limit strain according to the present invention, stretch flange limit strain is specified so as to satisfy a relation of a following Formula (1) by using: strain gradient in an inward direction from an end portion of a metal sheet (strain gradient in a radial direction in the case of a hole expansion test) when a press load is applied; and strain gradient in a sheet thickness direction of the metal sheet intersecting a loading direction.

$$\epsilon_{\theta lim} = A[a \cdot \Delta\epsilon_\theta / \Delta r + b \cdot \Delta\epsilon_\theta / \Delta t] + c \quad (1)$$

Note that, in the Formula (1), $\epsilon_\theta$ represents strain in a circumferential direction (stretch flange strain) of a hole edge portion, $\epsilon_{\theta lim}$ represents the stretch flange limit strain, $\Delta\epsilon_\theta/\Delta r$ represents the strain gradient in the inward direction (strain gradient in the radial direction), $\Delta\epsilon_\theta/\Delta t$ represents the strain gradient in the sheet thickness direction, A, a, and b represent influence coefficients, and c represents limit strain in the case where the strain gradient is zero.

In the following, detailed background of the present invention will be described.

Figure 19:
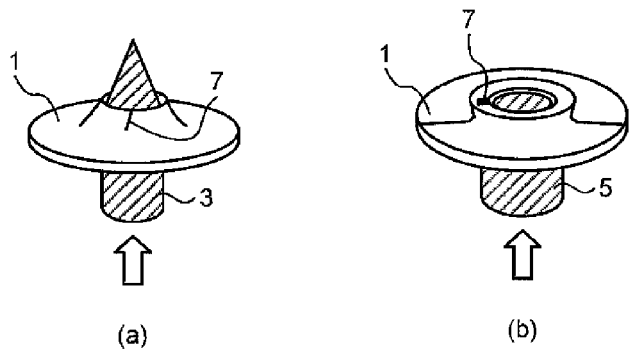
Figure 20:
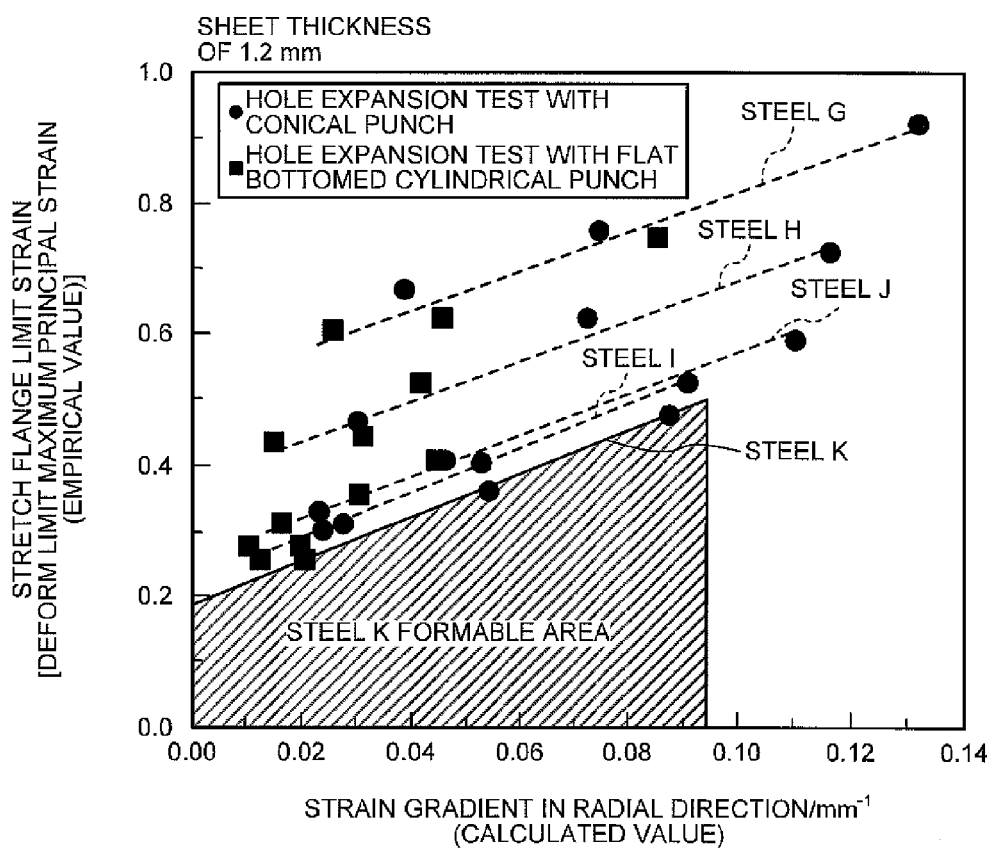
FIG. 20 is an exemplary graph of the hole expansion test result or the like, in which the horizontal axis is set according to the method in the related art (strain gradient in a radial direction).

Since the stretch flange limit strain and the strain gradient are obtained by executing the hole expansion test, a procedure of the hole expansion test according to the present embodiment will be described before describing the background of the present invention. In the hole expansion test according to the present embodiment, a hole having a predetermined diameter is preliminarily formed on a metal sheet 1 to be a test piece, and a punch is pushed up from a lower surface to an upper surface side of the metal sheet 1 while matching a center of the hole with a center of a punch (conical punch 3 and flat bottomed cylindrical punch 5), thereby expanding the diameter of the hole. Further, a crack 7 is generated at a hole edge portion by continuously pushing up the punch (refer to FIG. 19(a) in the case of the conical punch 3, and refer to FIG. 19(b) in the case of the flat bottomed cylindrical punch 5), an amount of strain in the circumferential direction of the hole (stretch flange limit strain) at this point is measured.

The reason for executing the hole expansion test with the flat bottomed cylindrical punch 5 and the conical punch 3 is that both of a deformation mode by the hole expansion using the flat bottomed cylindrical punch 5 and a deformation mode by the hole expansion using the conical punch 3 are typical deformation modes. The hole expansion using the flat bottomed cylindrical punch 5 corresponds to forming a stretch flange in deep drawing. On the other hand, the hole expansion using the conical punch 3 corresponds to flange up in crash forming.

In actual press forming, there are various kinds of forming modes for respective portions of press-formed parts, but any portion can be deemed as intermediate forming between the deep drawing and the crash forming. Therefore, examining a fracture limit by executing the hole expansion test with the flat bottomed cylindrical punch 5 and the conical punch 3 is important in order to create a unified index that can be applied to any kinds of press forming.

As a method other than the forming methods such as the deep drawing and the crash forming, there is a burring method frequently applied to automobile suspension parts. The burring method is a processing method used in the case of increasing thickness of a thin sheet, whereby hole expansion using the conical punch is further continued in a conical hole expansion test to erect a wall to increase the thickness. In this case, the hole edge is a stretch flange itself, and therefore, in the case where the above burring method is accompanied, the index obtained by examining the fracture limit with the above-described conical punch 3 is obviously applicable.

Figure 3:
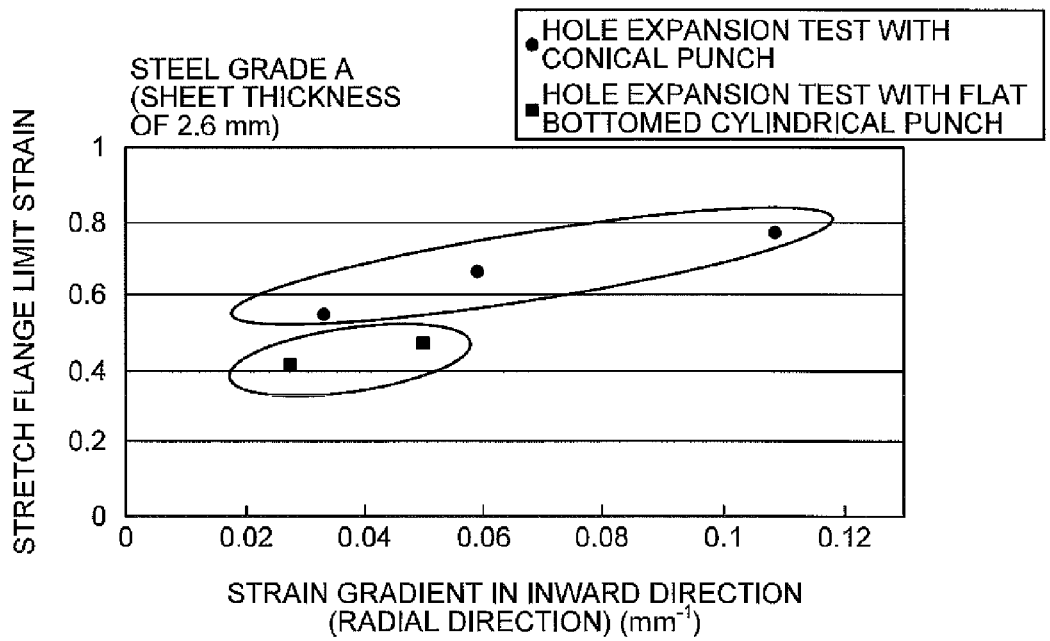
FIG. 3 is a graph in which the horizontal axis of FIG. 1 is set in accordance with a method in a related art (strain gradient in the radial direction).
Figure 4:
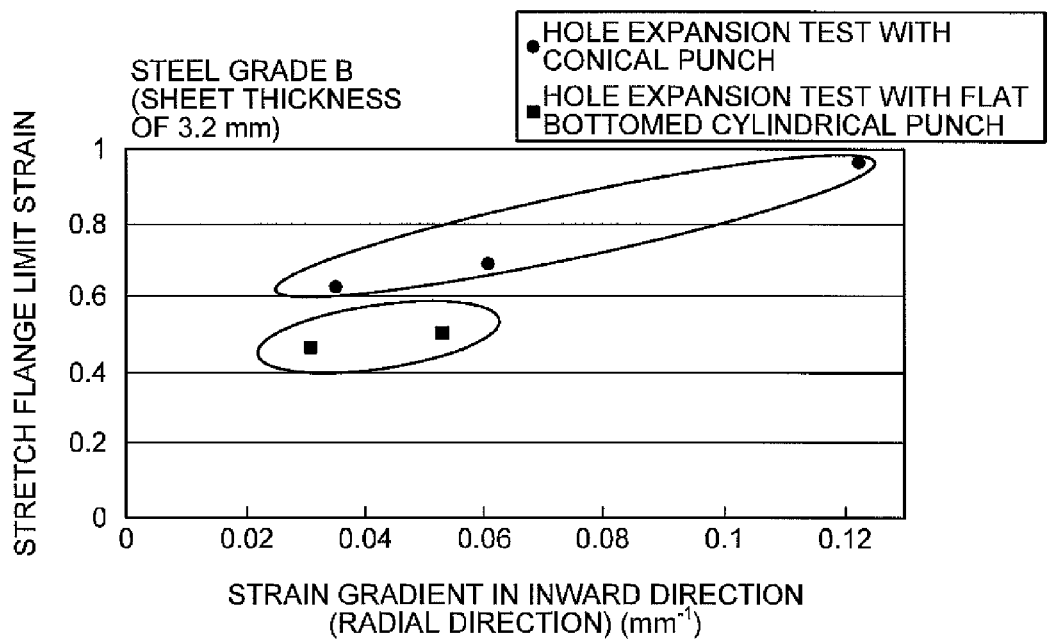
FIG. 4 is a graph in which the horizontal axis of FIG. 2 is set in accordance with the method in the related art (strain gradient in the radial direction).

FIGS. 3 and 4 are graphs in which the hole expansion test results are graphed by, same as the method in Patent Literature 1, a relation between the stretch flange limit strain and the strain gradient in the inward direction, namely, in the radial direction from the end portion of the metal sheet. FIG. 3 is the graph in which results of hole expansion tests executed on a metal sheet including steel grade A having the sheet thickness of 2.6 mm by using the conical punch 3 and the flat bottomed cylindrical punch 5 are graphed. FIG. 4 is the graph in which results of the hole expansion tests executed on the metal sheet including steel grade B having the sheet thickness of 3.2 mm by using the conical punch 3 and the flat bottomed cylindrical punch 5 are graphed. In FIGS. 3 and 4, a vertical axis represents the stretch flange limit strain, and a horizontal axis represents strain gradient ($mm^{-1}$) in the inward direction (radial direction).

As illustrated in FIGS. 3 and 4, the hole expansion test result using the conical punch and the hole expansion test result using the flat bottomed cylindrical punch form different groups respectively, and a stretch flange limit strain curve cannot be defined. Therefore, a crack of the stretch flange cannot be correctly predicted based on the results illustrated in FIGS. 3 and 4.

Further, the group of the hole expansion test result using the conical punch is located on a relatively more upper side of the graph than the group of the hole expansion test result using the flat bottomed cylindrical punch. This means that fracture hardly occurs in the case of executing the hole expansion test with the conical punch 3. The reason why the above difference between the hole expansion test results is thus caused by the difference of the shapes of the hole expanding punches (flat bottomed cylindrical punch 5 and conical punch 3) is, presumably, the deformation modes on the metal sheet are different. This point will be described below in detail.

First, fracture will be described. A state determined as fracture at a sheet edge in the process of stretch flange forming is a relatively macro phenomenon. For example, when a certain portion at the sheet edge reaches a state of exceeding a fracture limit, it can be considered that an origin of a micro crack is generated at the certain portion, and the crack is developed in the sheet thickness direction and the inward direction (radial direction), thereby causing fracture. Development of the crack is a quite fast phenomenon, and the crack is instantly developed and observed as the fracture when the state of the fracture limit is developed from the sheet edge to a portion in the sheet thickness direction and the inward direction (radial direction) to some extent after the certain portion of the sheet edge reaches the fracture limit.

Conversely, even though the certain portion at the sheet edge exceeds the fracture limit, when a portion adjacent to the certain portion does not exceed the fracture limit, i.e., has high extra deformability, the certain portion is protected by the adjacent portion and prevented from being instantly fractured (protective action). The direction, either the sheet thickness direction or the inward direction (radial direction), in which the crack 7 is preferentially developed is varied by material characteristics and sheet thickness conditions (refer to FIG. 19).

Figure 5:
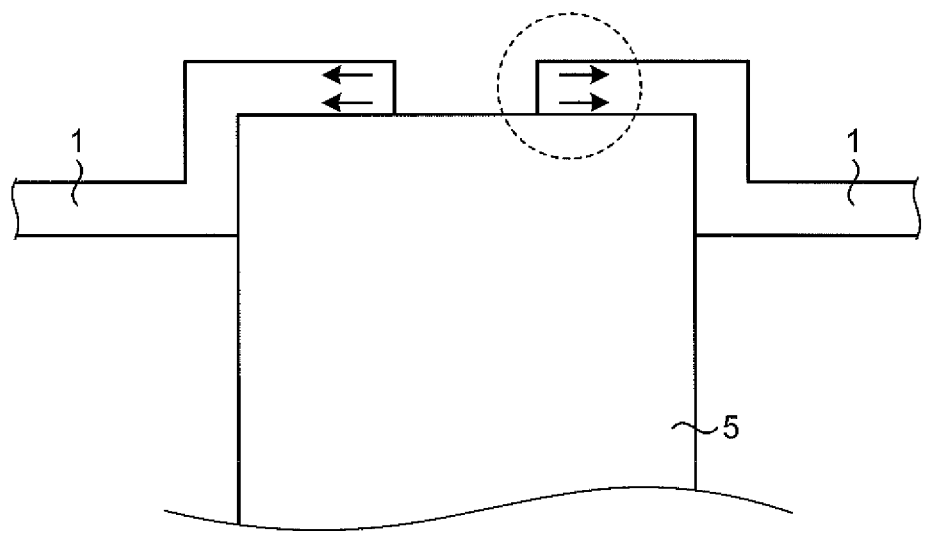
FIG. 5 is an explanatory diagram for describing a hole expansion test using a flat bottomed cylindrical punch according to the first embodiment of the present invention.
Figure 5:
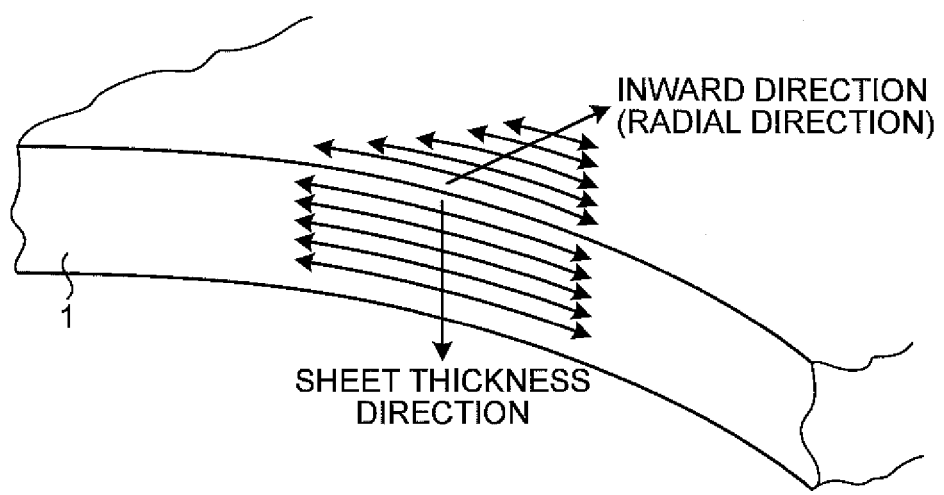
Figure 6:
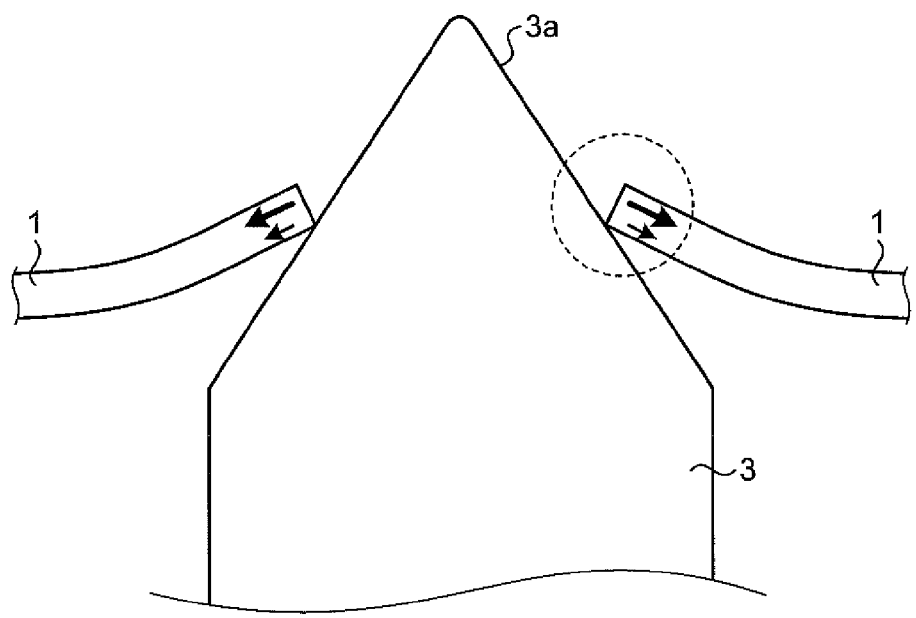
FIG. 6 is an explanatory diagram for describing the hole expansion test using a conical punch according to the first embodiment of the present invention.
Figure 6:
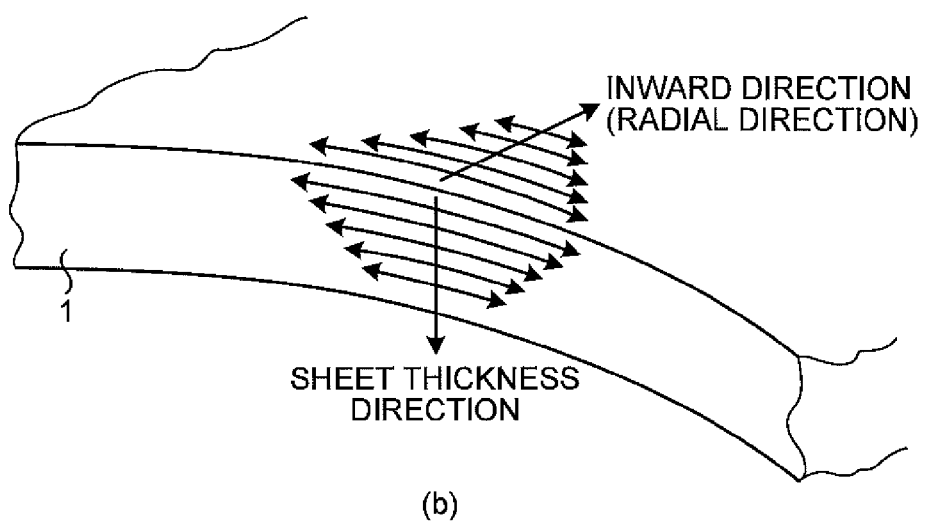

The deformation mode at the metal sheet 1 in the hole expansion test will be described considering this point based on FIGS. 5 and 6. FIG. 5(*a*) is a cross-sectional view illustrating a deformation mode at the metal sheet 1 in the sheet thickness direction when the hole expansion test is executed using the flat bottomed cylindrical punch 5, and FIG. 5(*b*) is an enlarged view of a portion encircled by a dotted line at the hole edge portion in FIG. 5(*a*). FIG. 6(*a*) is a cross-sectional view illustrating the deformation mode at the metal sheet 1 in the sheet thickness direction when the hole expansion test is executed using the conical punch 3, and FIG. 6(*b*) is an enlarged view illustrating a part of the hole edge portion in FIG. 6(*b*). In FIGS. 5(*b*) and 6(*b*), a length of an arrow directed to both directions represents the amount of strain in the circumferential direction.

In the case of using the flat bottomed cylindrical punch 5, the diameter of the hole edge portion is expanded in a manner being pulled by a corner portion of the flat bottomed cylindrical punch 5 in a radially outer direction (deformation in an in-plane direction) as illustrated in FIG. 5(*a*). At this point, the hole edge portion is uniformly pulled in the radially outer direction as illustrated by an arrow in FIG. 5(*a*). Therefore, the amount of strain in the sheet thickness direction of the hole edge portion is uniform, in other words, there is almost no strain gradient in the sheet thickness direction (refer to FIG. 5(*b*)). The amount of strain in the inward direction (radial direction) is not uniform, and the strain gradient in the inward direction (radial direction) is steep.

On the other hand, in the case of using the conical punch 3, the diameter of the hole is expanded in a manner being pushed in a direction to the apex of the conical punch 3 by an inclined portion 3*a* at the apex of the conical punch 3 as illustrated in FIG. 6(*a*) (deformation in an off-plane direction). An upper surface side of the metal sheet is located on a radially more outer side than a lower surface side contacting the conical punch 3 by an amount of sheet thickness. Therefore, the upper surface is extended by the amount. In contrast, the lower surface side of the metal sheet is not much extended (refer to the arrows in FIG. 6(*a*)). For this reason, the strain gradient in the sheet thickness direction is relatively steeper than the case of the flat bottomed cylindrical punch 5 (refer to FIG. 6(*b*)). In other words, the lower surface side has the higher extra deformability (protective effect) than the upper surface side. The strain gradient in the inward direction (radial direction) is also a steep gradient same as the case of the flat bottomed cylindrical punch 5.

In the case where the strain gradient in the sheet thickness direction is thus large like the case of using the conical punch 3, the protective effect by the portion having the high extra deformability (portion having a small amount of strain) becomes large. Therefore, even when the relation between the strain gradient in the inward direction (radial direction) and the stretch flange strain reaches the fracture limit, an entire portion of the metal sheet does not reach the fracture limit, and fracture does not instantly penetrate in the sheet thickness direction. Therefore, as illustrated in FIGS. 3 and 4, the group of the hole expansion test result using the conical punch is higher than the group of the hole expansion test result using the flat bottomed cylindrical punch by the amount of protective effect at the portion on the lower surface side of the metal sheet.

As described above, in the case of the metal sheet 1 having the large sheet thickness, both the strain gradient in the inward direction (radial direction) and the strain gradient in the sheet thickness direction affect the stretch flange limit strain.

In the case of mathematically expressing the above-described relation between the stretch flange limit strain and the strain gradient, a description will be provided as follows. The general relation between the stretch flange limit strain $\epsilon_{\theta lim}$, and the strain gradient dx is expressed by Formula (2) as follows.

$$\epsilon_{\theta lim} = A \cdot dx + c \tag{2}$$

As described above, since the stretch flange limit strain is affected by both the strain gradient in the inward direction (radial direction) and the strain gradient in the sheet thickness direction, overlap of the strain gradient dx in the inward direction (radial direction) on the strain gradient in the sheet thickness direction is expressed by Formula (3) as follows.

$$dx = a \cdot \epsilon_\theta / \Delta r + b \cdot \Delta \epsilon_\theta / \Delta t \tag{3}$$

The above-described Formula (1) shown below is obtained by plugging in the Formula (3) for the Formula (2) and arranging the same.

$$\epsilon_{\theta lim} = A[a \cdot \Delta \epsilon_\theta / \Delta r + b \cdot \Delta \epsilon_\theta / \Delta t] + c \tag{1}$$

Note that, in the Formula (1), $\epsilon_\theta$ represents the strain (strain of the stretch flange) in the circumferential direction of the hole edge portion, $\epsilon_{\theta lim}$ represents the stretch flange limit strain, $\Delta \epsilon_\theta / \Delta r$ represents the strain gradient in the inward direction (radial direction), $\Delta \epsilon_\theta / \Delta t$ represents the strain gradient in the sheet thickness direction, A, a, and b represent the influence coefficients, and c represents the limit strain in the case where the strain gradient is zero.

Alternately, the Formula (1) may be further generalized as Formula (4) shown below.

$$\epsilon_{\theta lim} = a' \cdot \{\Delta \epsilon_\theta / \Delta r\}^n + b' \cdot \{\Delta \epsilon_\theta / \Delta t\}^m + c \tag{4}$$

Note that, in the Formula (4), a', b', n, and m represent influence coefficients, and other variable numbers are same as the Formula (1). In the case of setting n=1 and m=1 in the Formula (4), the Formula (1) is obtained.

Parameters (A, a, b, c, a', b', n, and m) in the Formula (1) and Formula (4) can be determined by executing the hole expansion tests under various kinds of conditions (steel grade, sheet thickness, piercing, and clearance in shearing). A safety factor may be suitably set for a created limit curve, considering possibility of occurrence of variations by manufacturing lots even in the case of the same metal sheet (same steel grade, same sheet thickness, or the like).

The strain gradient in the sheet thickness direction can be obtained by an actual hole expansion test. More specifically, minute and accurate marks that can be traced before and after execution of stretch flange forming are put on both surfaces of the test piece, and the amount of strain is measured based on a positional difference between the marks on the both surface after the test. Then, the strain gradient can be calculated by dividing a difference of the amount of strain between the front and back surfaces by the sheet thickness.

Further, as a different method, the strain gradient in the sheet thickness direction can be also obtained by simulating the hole expansion test by the FEM analysis using a solid element. In this case, the strain gradient in the sheet thickness direction can be obtained with sufficient accuracy by dividing the element into five or more sections in the sheet thickness direction. Also, in the case where decrease of accuracy is allowable to some extent, the strain gradient in the sheet thickness direction can be also obtained by setting at least five integration points in the sheet thickness direction, using a shell element. The strain gradient in the inward direction (radial direction) and the strain gradient in the sheet thickness direction can be changed by changing an initial hole diameter, a shape of the hole expanding punch, size of the industrial tool at the time of the hole expansion test.

As described above, the stretch flange limit strain can be specified so as to satisfy the Formula (1) or (4) by using: the strain gradient in the inward direction from the end portion of the metal sheet (strain gradient in the radial direction in the case of a hole expansion test) when the press load is applied; and the strain gradient in the sheet thickness direction of a metal sheet intersecting the loading direction.

Figure 1:
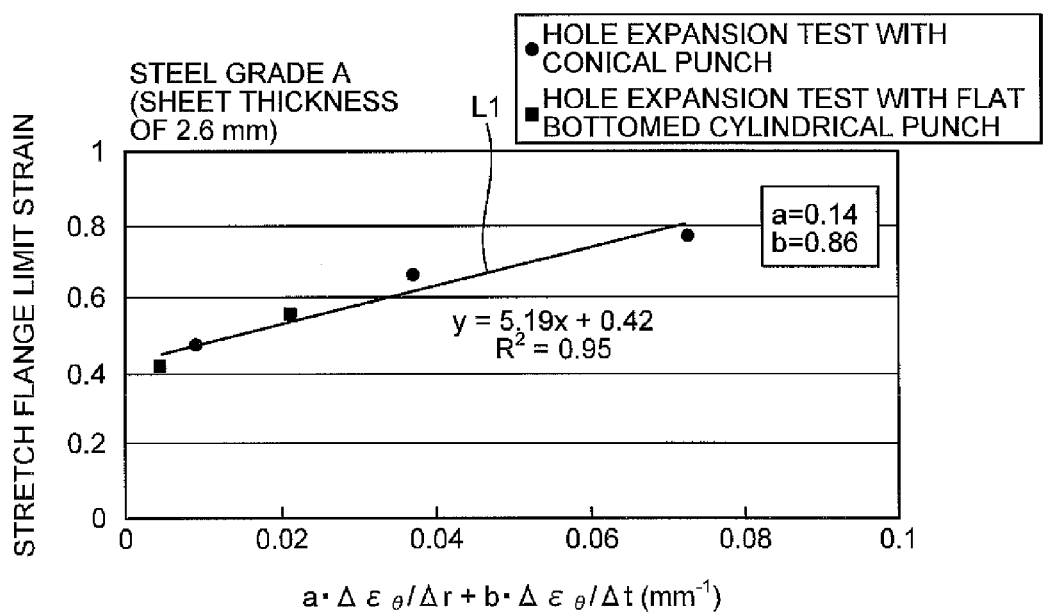
FIG. 1 is an exemplary graph of a hole expansion test result according to a first embodiment of the present invention (steel grade A), in which a vertical axis represents stretch flange limit strain and a horizontal axis represents a value obtained by overlapping strain gradient in a radial direction on strain gradient in a sheet thickness direction.
Figure 2:
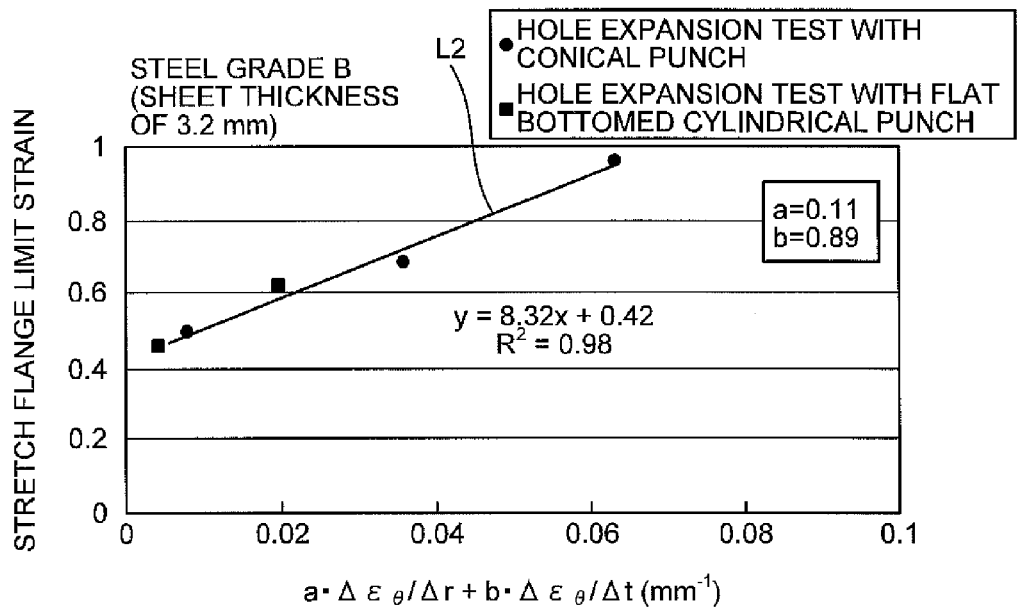
FIG. 2 is an exemplary graph of the hole expansion test result according to the first embodiment of the present invention (steel grade B), in which the vertical axis represents stretch flange limit strain and the horizontal axis represents a value obtained by overlapping the strain gradient in the radial direction on the strain gradient in the sheet thickness direction.

Further, in FIGS. 3 and 4, the strain gradient in the radial direction is set as the horizontal axis in order to graph the relation between the stretch flange limit strain and the strain gradient, but the relation between the stretch flange limit strain and the strain gradient can be graphed more correctly by setting, as the horizontal axis, the value obtained by adding the strain gradient in the radial direction with the strain gradient in the sheet thickness direction instead. FIGS. 1 and 2 illustrate the graphs in which the hole expansion test results illustrated in FIGS. 3 and 4 are newly plotted by setting, as the horizontal axis, the value ($a \cdot \Delta\epsilon_\theta/\Delta r + b \cdot \Delta\epsilon_\theta/\Delta t$) ($mm^{-1}$) obtained by adding the strain gradient in the radial direction with the strain gradient in the sheet thickness direction.

In FIG. 1, approximation curve L1 created based on the respective test results is expressed by a formula: $y=5.19x+0.42$ (an example of an empirical formula according to the present invention). A value $R^2$ of a coefficient of determination is provided as an index to indicate how approximate to each data approximation curve is, and it indicates that the closer to 1 the value $R^2$ is, the more approximation curve achieves to approximate each data. In the case of approximation curve L1, the value $R^2$ is 0.95. This means that approximation curve L1 is quire approximate to the hole expansion test result using the flat bottomed cylindrical punch and the hole expansion test result using the conical punch.

Therefore, in the case of using approximation curve L1 in FIG. 1 as the stretch flange limit strain curve, a fracture limit value of the stretch flange at the metal sheet including the steel grade A and having the sheet thickness of 2.6 mm can be grasped based on the value obtained by adding the strain gradient in the radial direction with the strain gradient in the sheet thickness direction, regardless the difference of the shape of the hole expanding punch.

FIG. 2 will be described in the same manner. Approximation curve L2 in FIG. 2 created based on the respective test results is expressed by an empirical formula: $y=8.32x+0.42$ (an example of the empirical formula according to the present invention). The value $R^2$ of approximation curve L2 is 0.98, and approximation curve L2 is quite approximate to the respective test results. Therefore, approximation curve L2 in FIG. 2 also can be used as the stretch flange limit strain curve for the metal sheet including the steel grade B and having the sheet thickness of 3.2 mm same as above approximation curve L1.

As described above, the value ($a \cdot \Delta\epsilon_\theta/\Delta r + b \cdot \Delta\epsilon_\theta/\Delta t$) ($mm^{-1}$) obtained by adding the strain gradient in the radial direction with the strain gradient in the sheet thickness direction is set as the horizontal axis in the case of graphing the relation between the stretch flange limit strain and the strain gradient, thereby achieving to predict the stretch flange limit strain with high accuracy in press forming a metal sheet having large sheet thickness.

Meanwhile, in the case of a high-strength metal sheet of particularly 590 MPa class or higher, influence of the strain gradient in a tangential direction of the hole edge portion resulted in small.

In the case of executing press forming to a predetermined metal sheet by obtaining the stretch flange limit strain for the metal sheet specified in the above-described manner, it is possible to determine whether crack occurs (determination on feasibility of press forming).

In the following, a procedure of a method for determining feasibility of press forming will be described.

According to the method for determining feasibility of press forming, first the stretch flange limit strain at a sheared edge is obtained by executing hole expansion tests using a metal sheet including a predetermined steel grade and having a predetermined sheet thickness (stretch flange limit strain acquiring step) while changing the initial hole diameter and the shape of the hole expanding punch (conical punch, flat bottomed cylindrical punch, or the like).

Next, the strain gradient in the radial direction of the initial hole near the sheared edge after the hole expansion test is obtained (detecting step for strain gradient in the radial direction). In the same manner, the strain gradient in the sheet thickness direction near the sheared edge after the hole expansion test is obtained (detecting step for strain gradient in the sheet thickness direction).

Next, the stretch flange limit strain obtained in the above stretch flange limit strain acquiring step, the strain gradient in the radial direction obtained in the detecting step for the strain gradient in the radial direction, and the strain gradient in the sheet thickness direction in the detecting step for the strain gradient in the sheet thickness direction are used to obtain an empirical formula representing the relation between the stretch flange limit strain and the [$a \cdot \Delta\epsilon_\theta/\Delta r + b \cdot \Delta\epsilon_\theta/\Delta t$] obtained by adding the strain gradient in the radial direction with the strain gradient in the sheet thickness direction. Then, by using the empirical formula, feasibility of press forming that causes strain of the stretch flange is determined (determining step).

More specifically, determination is made by comparing the stretch flange strain caused by press forming with the stretch flange limit strain acquired by using the empirical formula. In the case where the stretch flange strain is smaller than the stretch flange limit strain, it is determined that press forming can be executed. On the other hand, in the case where the stretch flange strain exceeds the stretch flange limit strain, it is determined that press forming cannot be executed. Actually, it is decided that from the limit curve, the crack occurs. Further, preferably, the safety factor may be provided, considering variations of the used material as described above, variations in the manufacturing process such as a slight change in deformation behavior at the time of pressing. More specifically, the stretch flange limit strain used in the determining step is set at a lower value compared with the stretch flange limit strain acquired in the stretch flange limit strain acquiring step.

Second Embodiment

According to a first embodiment described above, a case of considering both strain gradient in an inward direction (radial direction) and strain gradient in a sheet thickness direction has been described, but depending on a steel grade, tests were executed based on a presumption that only the strain gradient in the sheet direction is to be considered. Therefore, a result thereof will be described below.

The tests were performed for metal sheets (sheet thickness of 2.6 mm) including three kinds of steel grades (steel grade C to steel grade E) having different compositions and structures by executing hole expansion tests using a conical punch and a flat bottomed cylindrical punch in the same manner as the first embodiment. The sizes of holes before the tests were set at 10 mm φ, 20 mm φ, 25 mm φ, and 50 mm φ.

Figure 7:
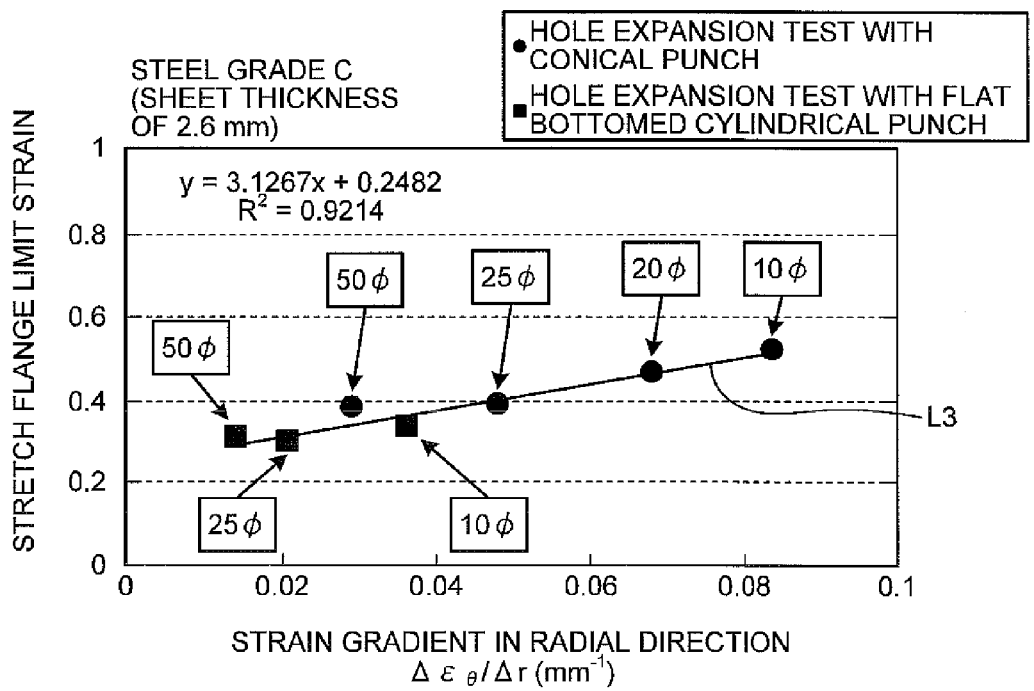
FIG. 7 is an exemplary graph of a hole expansion test result according to the method in the related art illustrated in a second embodiment (steel grade C), in which the vertical axis represents the stretch flange limit strain and the horizontal direction represents the strain gradient in the radial direction.
Figure 8:
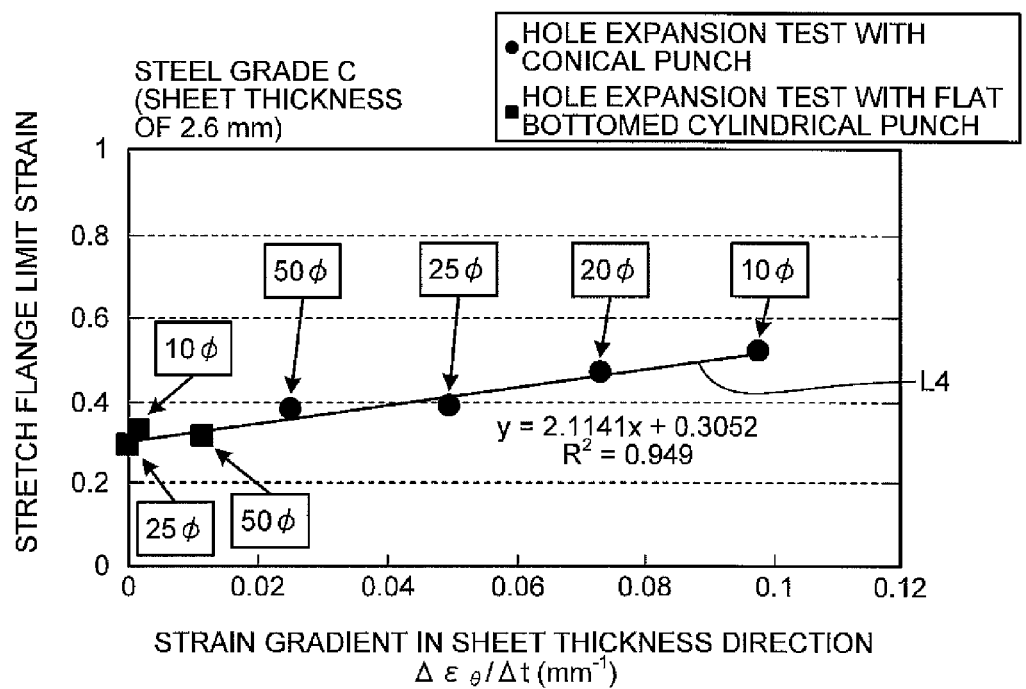
FIG. 8 is a graph illustrating a method according to the present invention, in which the horizontal axis of the graph in FIG. 7 is set as the strain gradient in the sheet thickness direction.
Figure 9:
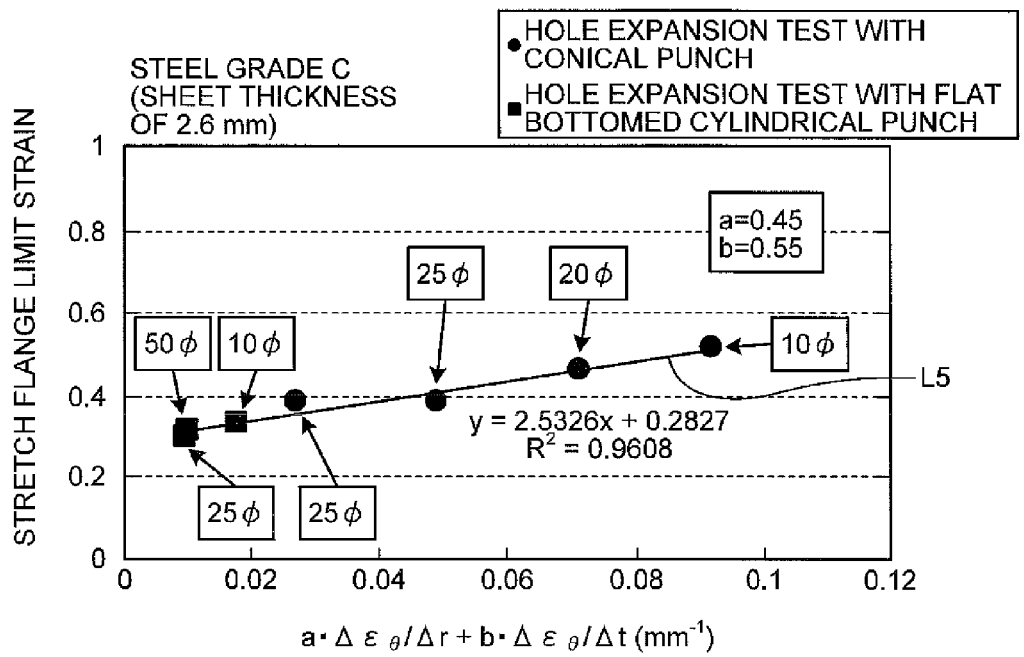
FIG. 9 is a graph illustrating the method according to the present invention, in which the horizontal axis in FIG. 7 represents the value obtained by overlapping the strain gradient in the radial direction on the strain gradient in the sheet thickness direction.

FIGS. 7 to 9 illustrate results of the hole expansion tests executed for the metal sheet including the steel grade C. In FIGS. 7 to 9, vertical axes commonly represent stretch flange limit strain, and only horizontal axes are differently set. The horizontal axis in FIG. 7 represents strain gradient in a radial direction ($mm^{-1}$), the horizontal axis in FIG. 8 represents strain gradient in a sheet thickness direction ($mm^{-1}$), and the horizontal axis in FIG. 9 represent a value ($a \cdot \Delta\epsilon_\theta/\Delta r + b \cdot \Delta\epsilon_\theta/\Delta t$) ($mm^{-1}$) obtained by adding the strain gradient in the radial direction with the strain gradient in the sheet thickness direction. As for influence coefficients a and b, an optimal value can be obtained, for example, as a+b=1.

Referring to FIG. 7, a value $R^2$ of a coefficient of determination in approximation curve L3 is 0.9214 which is a high value, but the value $R^2$ in approximation curve L4 in FIG. 8 is 0.949 which is higher, and further, the value $R^2$ in approximation curve L5 in FIG. 9 is 0.9608 which is the highest. As described above, the closer to 1 the value $R^2$ of the approximation curve is, the more respective test results are approximated by the approximation curve and the stretch flange limit strain can be predicted with high accuracy. The stretch flange limit strain can be predicted with the highest accuracy in the case of considering both of the strain gradient in the radial direction and the strain gradient in the sheet thickness direction, but can be also predicted with sufficiently high accuracy in the case of considering only the strain gradient in the sheet thickness direction.

Figure 10:
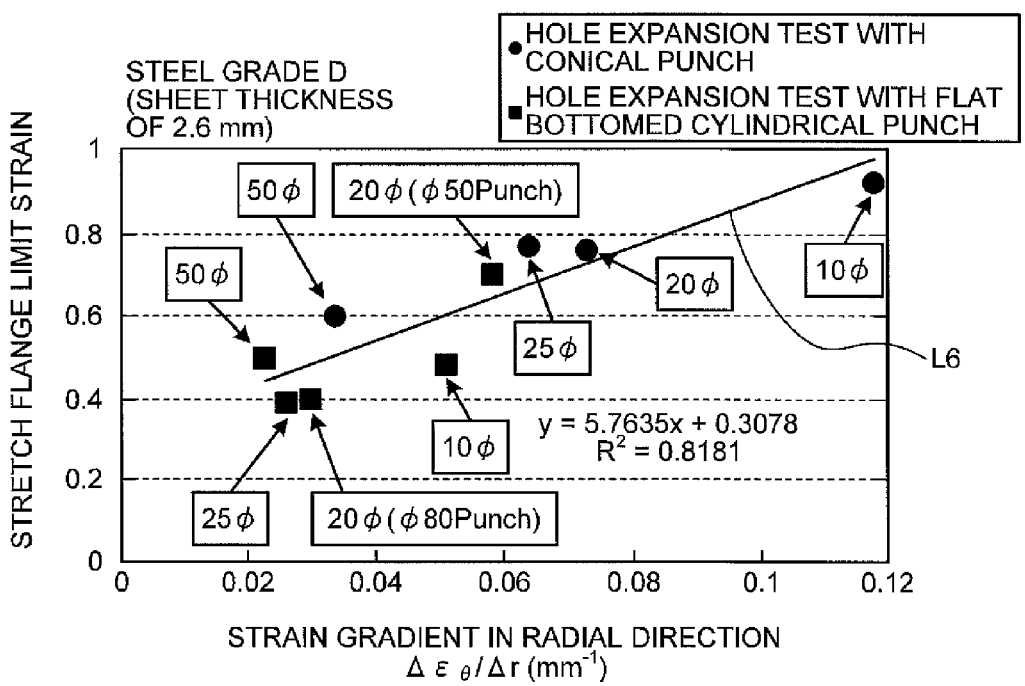
FIG. 10 is an exemplary graph of the hole expansion test result in the related art illustrated in the second embodiment (steel grade D), in which the vertical axis represents the stretch flange limit strain and the horizontal axis represents the strain gradient in the radial direction.
Figure 11:
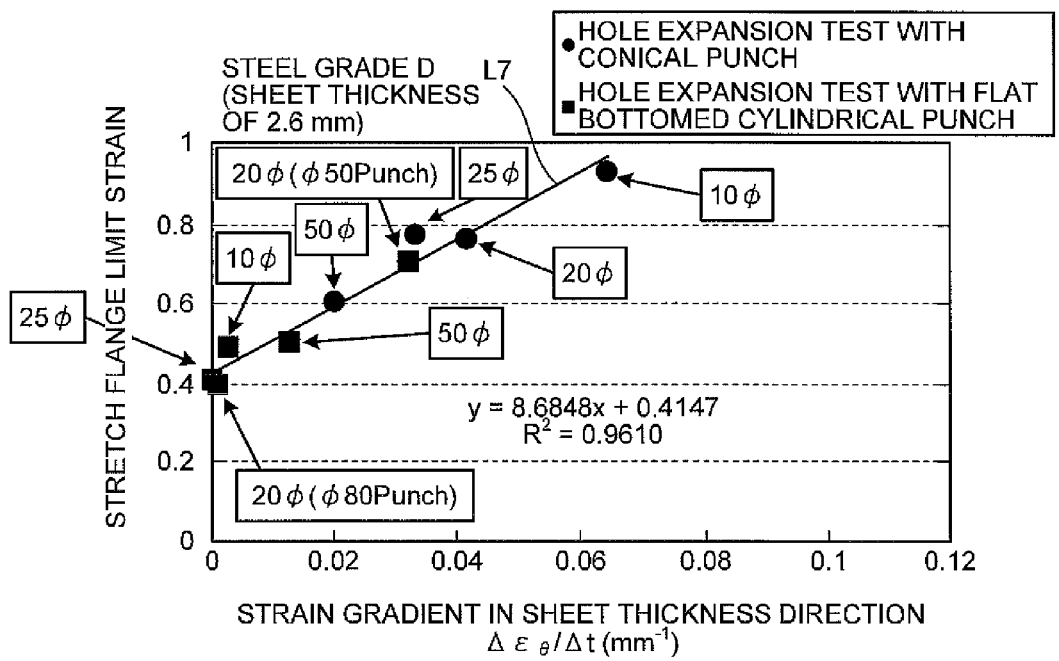
FIG. 11 is a graph illustrating the method according to the present invention, in which the horizontal axis of the graph in FIG. 10 is set as the strain gradient in the sheet thickness direction.
Figure 12:
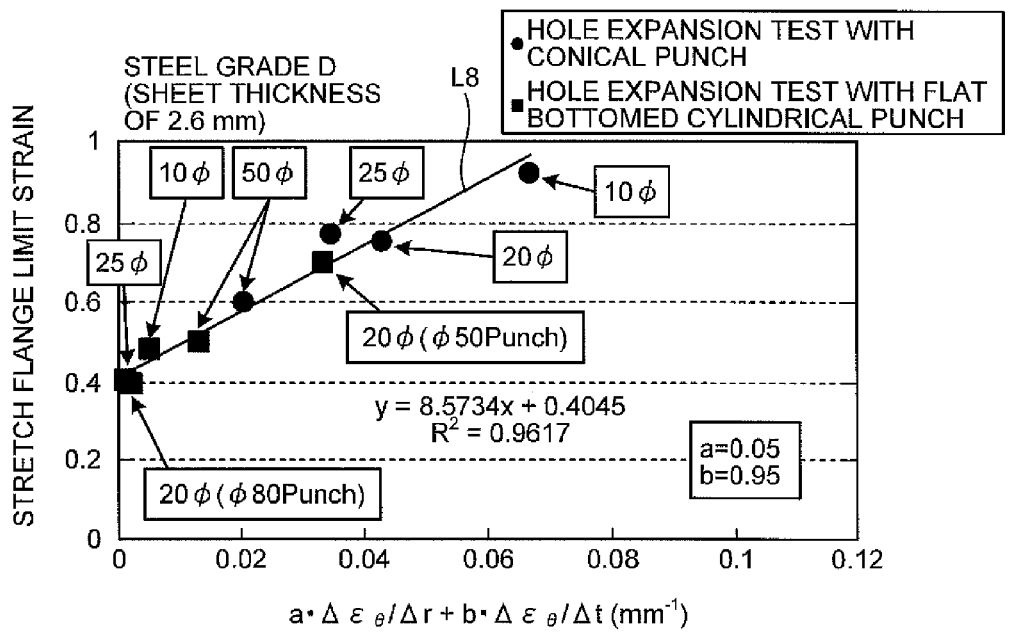
FIG. 12 is a graph illustrating the method according to the present invention, in which the horizontal axis of the graph in FIG. 10 represents the value obtained by overlapping the strain gradient in the radial direction on the strain gradient in the sheet thickness direction.

FIGS. 10 to 12 are results of the hole expansion tests executed for the metal sheet including the steel grade D, and the way of reading the drawings is same as FIGS. 7 to 9. Therefore, a description therefor will be omitted. In the case of setting the strain gradient in the radial direction as the horizontal axis, the value $R^2$ in approximation curve L6 is 0.8181 which is rather low as illustrated in FIG. 10. On the other hand, in the case of setting the strain gradient in the sheet thickness direction as the horizontal axis, the value $R^2$ in approximation curve L7 is 0.9610 as illustrated in FIG. 11. In the case of setting, as the horizontal axis, the value obtained by adding the strain gradient in the radial direction with the strain gradient in the sheet thickness direction, the value $R^2$ in approximation curve L8 is 0.9617 which is the highest value as illustrated in FIG. 12. Thus, accuracy is best in the case of setting, as the horizontal axis, the value obtained by adding the strain gradient in the radial direction with the strain gradient in the sheet thickness direction, but the stretch flange limit strain can also be predicted with sufficiently high accuracy in the case of setting the strain gradient in the sheet thickness as the horizontal axis.

Figure 13:
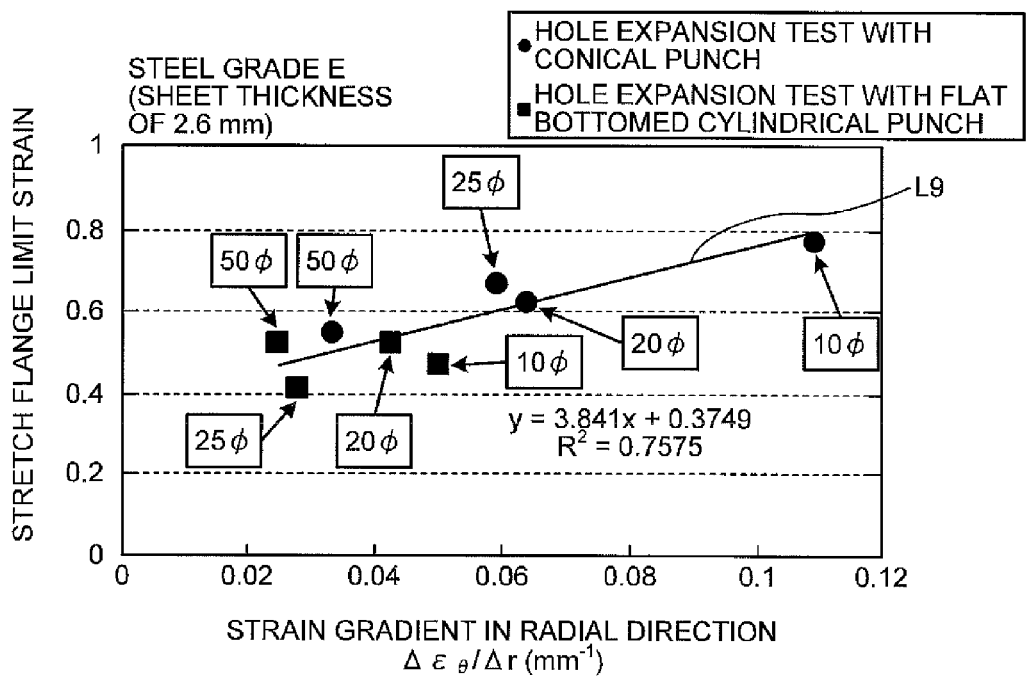
FIG. 13 is an exemplary graph of the hole expansion test result in the related art illustrated in the second embodiment (steel grade E), in which the vertical axis represents the stretch flange limit strain and the horizontal axis represents the method in the related art (strain gradient in the radial direction).
Figure 14:
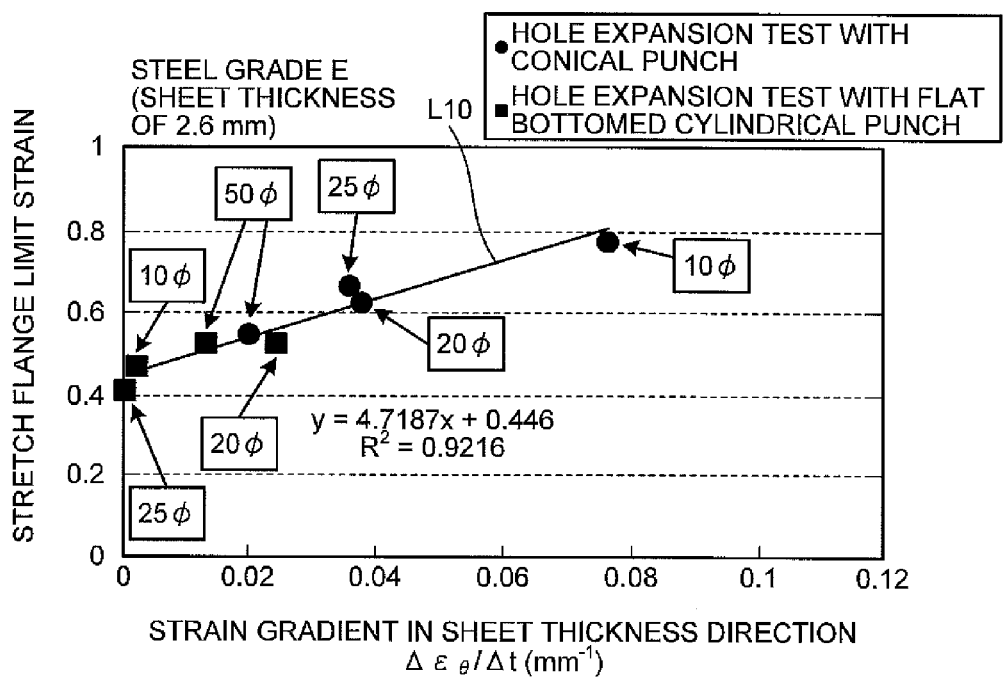
FIG. 14 is a graph illustrating the method according to the present invention, in which the horizontal axis of the graph in FIG. 13 is set as the strain gradient in the sheet thickness direction.
Figure 15:
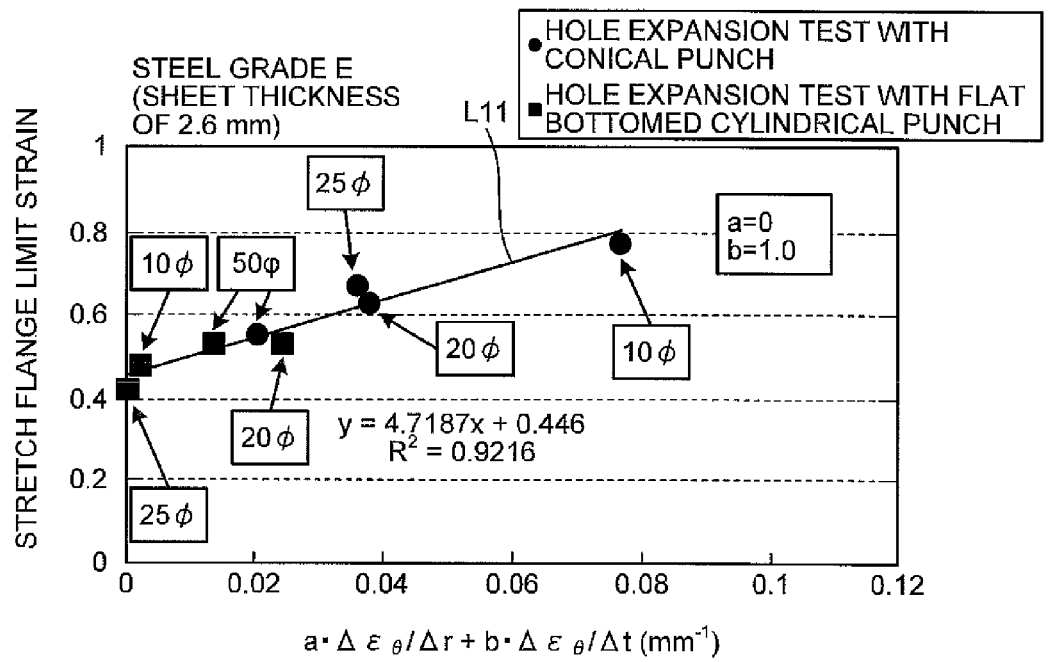
FIG. 15 is a graph illustrating the method according to the present invention, in which the horizontal axis of the graph in FIG. 13 represents the value obtained by overlapping the strain gradient in the radial direction on the strain gradient in the sheet thickness direction.

FIGS. 13 to 15 illustrates results of the hole expansion tests executed for the metal sheet including steel grade E. In the case of setting, as the horizontal axis, the strain gradient in the radial direction, the value $R^2$ in approximation curve L9 is 0.7575 which is low as illustrated in FIG. 13. However, in the case of setting the strain gradient in the sheet thickness direction as the horizontal axis, the value $R^2$ in approximation curve L10 is 0.9216 which is high as illustrated in FIG. 14. In the case of setting, as the horizontal axis, the value obtained by adding the strain gradient in the radial direction with the strain gradient in the sheet thickness direction, the value $R^2$ in approximation curve L11 is 0.9216 because an optimal value of the influence coefficient a in the radial direction is zero as illustrated in FIG. 15. Consequently, the result turned out to be same as the case in FIG. 14.

As described above, the stretch flange limit strain can be predicted with the highest accuracy in the case of considering both of the strain gradient in the radial direction and the strain gradient in the sheet thickness. But, even in the case of considering only the strain gradient in the sheet thickness direction, the stretch flange limit strain can also be predicted with sufficiently high accuracy.

In the case of expressing a method of specifying the stretch flange limit strain only considering the strain gradient in the sheet thickness direction by a mathematical formula, it is only to set, to zero, the coefficient a of the strain gradient in the radial direction in Formula (1) in which both amounts in the radial directions and the sheet thickness directions are considered as described in the first embodiment. More specifically, the method can be expressed by following Formula (5) in which the coefficient a in the Formula (1) is set at zero.

$$\epsilon_{\theta lim} = A[b \cdot \Delta\epsilon_\theta/\Delta t] + c \quad (5)$$

Further, as a generalized Formula, Formula (6) can be obtained by setting a'=0 in Formula (4).

$$\epsilon_{\theta lim} = A[b \cdot \Delta\epsilon_\theta/\Delta t] + c \quad (5)$$

When the present invention is applied to stretch flange forming for the metal sheet having the sheet thickness of 2.0 mm or more, the stretch flange limit strain can be specified with higher accuracy.

Examples

Figure 16:
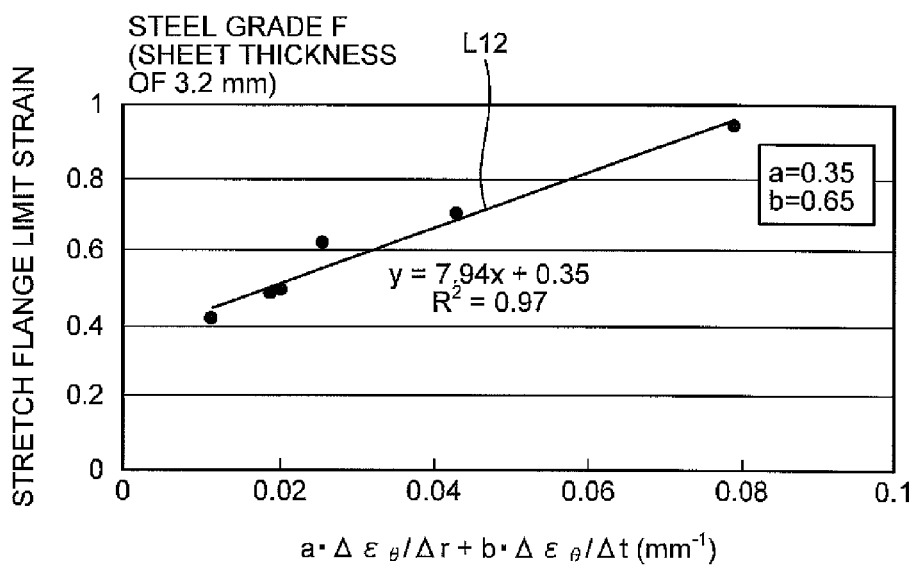
FIG. 16 is an exemplary graph of the hole expansion test result according to an example (steel grade F), in which the vertical axis represents the stretch flange limit strain and the horizontal axis represents the value obtained by overlapping the strain gradient in the radial direction on the strain gradient in the sheet thickness direction according to the present invention.
Figure 17:
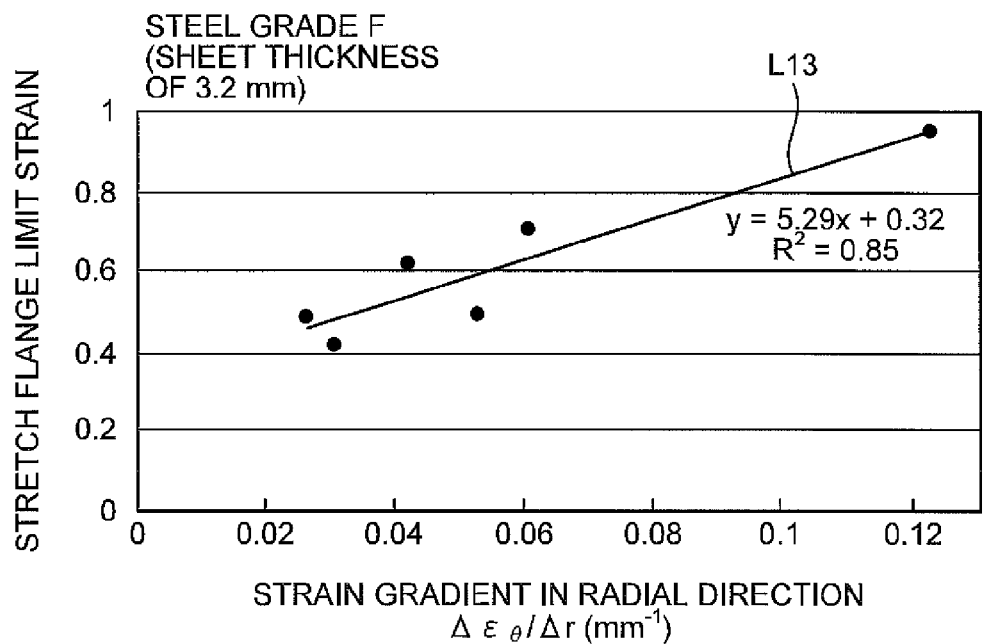
FIG. 17 is a graph illustrating the method in the related art, in which the horizontal axis of the graph in FIG. 16 is set as the strain gradient in the radial direction for comparison.
Figure 18:
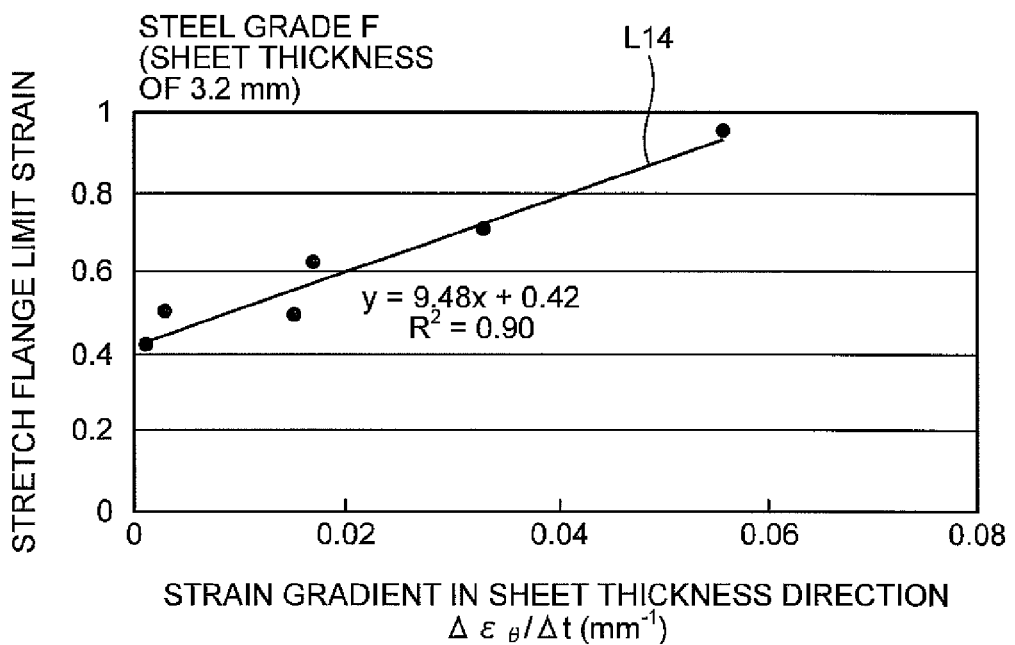
FIG. 18 is a graph illustrating another example of the present invention, in which the horizontal axis of the graph in FIG. 16 is set as the strain gradient in the sheet thickness direction.

Effects provided by the method for specifying the stretch flange limit strain according to the present invention will be described based on concrete examples. The description will be provided referring to FIGS. 16 to 18. FIGS. 16 to 18 are graphs in which results of hole expansion tests executed for a metal sheet including steel grade F having the sheet thickness of 3.2 mm by using the conical punch 3 and the flat bottomed cylindrical punch 5 are graphed, and only the horizontal axes are set differently. In FIGS. 16 to 18, the vertical axes represent the stretch flange limit strain. FIG. 16 is the graph as an example of the invention in which the horizontal axis represents the value ($a \cdot \Delta\epsilon_\theta/\Delta r + b \cdot \Delta\epsilon_\theta/\Delta t$) ($mm^{-1}$) obtained by adding the strain gradient in the radial direction with the strain gradient in the sheet thickness direction. FIG. 17 is the graph as a comparative example in which the horizontal axis represents the strain gradient in the radial direction ($\Delta\epsilon_\theta/\Delta r$) ($mm^{-1}$). Further, FIG. 18 is the graph as another example of the invention in which the horizontal axis represents the strain gradient in the sheet thickness direction ($\Delta\epsilon_\theta/\Delta t$) ($mm^{-1}$).

In FIG. 16, approximation curve L12 created based on respective test results is expressed by a formula: y=7.94x+0.35 (corresponding to the empirical formula of the first embodiment). The value $R^2$ of the coefficient of determination in approximation curve L12 is 0.97, and the approximation curve L12 is quite approximate to respective test results. On the other hand, approximation curve L13 created based on respective test results in FIG. 17 is expressed by a formula: y=5.29x+0.32, and the value $R^2$ was 0.85. Further, approximation curve L14 created based on respective test results in FIG. 18 is expressed by a formula: y=9.48x+0.42 (corresponding to the empirical formula in the second embodiment), and the value $R^2$ was 0.90.

Thus, the value $R^2$ in approximation curve L12 illustrated in FIG. 16 was the highest value, next the value $R^2$ in approximation curve L14 illustrated in FIG. 18 was high, and the value $R^2$ in approximation curve L13 illustrated in FIG. 17 was the lowest value. The reason why the value $R^2$ in approximation curve L14 is lower than the value $R^2$ in approximation curve L12 can be considered that influence of the strain gradient in the radial direction is large because the steel grade F is the steel grade easily causing a crack in the radial direction. But, it is already proved that the value $R^2$ is higher than the $R^2$ in approximation curve L13 in which only the radial direction is considered, and accuracy thereof is higher than accuracy of the method in the related art in which only the radial direction is considered.

As described above, approximation curve L12 (corresponding to the empirical formula in the first embodiment) is most approximate to the respective test results, and the stretch flange limit strain can be obtained with high accuracy based on the empirical formula representing approximation curve L12. Therefore, unfeasibility of press forming can be determined with high accuracy.

In the above description, an area near the sheared edge is set to calculate the strain gradient, and calculation is executed within the area. More specifically, the area having a size about twice the sheet thickness was set, the strain gradient in the radial direction was obtained by calculating the strain gradient in the inward direction from the sheet edge at the center of the sheet thickness, and an average value of the strain in the radial direction within the area was used as the strain gradient in the sheet thickness direction.

However, influence on calculation accuracy is varied by the materials when calculating the strain gradient in the setting area. Therefore, in the case of obtaining an empirical formula by suitably changing the setting area per material and using the obtained empirical formula to determine feasibility of press forming for an actual component, it is also preferable to determine feasibility by calculating the strain gradient in the same area. But, the inventors confirmed that the above method can be put into practice in most cases without deteriorating accuracy of the empirical formula by setting the area having the size about equal to the sheet thickness, the size about twice the sheet thickness, or the area having the size of a fixed value such as about 5 mm or 7 mm as the area where the strain gradient is calculated.

Further, both in the case of adopting the strain gradient in the sheet thickness direction at a portion nearest to the sheet edge (terminal edge) and in the case of adopting the average value within the area, the strain gradient in the sheet thickness direction has substantially same tendency in most cases. Therefore, in order to simplify the calculation, the strain gradient in the sheet thickness direction at the terminal edge may also be adopted. In this case also, the condition must to be the same between the case of obtaining the empirical formula and the case of determining feasibility of press forming for an actual component. More specifically, in the case of adopting the strain gradient in the sheet thickness direction at the terminal edge when obtaining the empirical formula, it is important to adopt the strain gradient in the sheet thickness direction at the terminal edge when determining feasibility of press forming for the actual component as well.

Further, it is not necessary to create the limit curve every time before determination when a limit curve is preliminarily acquired per steel grade and per sheet thickness to create a database and formability of stretch flange is determined for the actual component by using a database. In this case also, determination on a safer side is achieved by providing the limit curve with the safety factor, considering variation caused by respective material lots or the like.

INDUSTRIAL APPLICABILITY

According to the present invention, stretch flange limit strain can be predicted with high accuracy in the case of press forming a metal sheet having large sheet thickness.

REFERENCE SIGNS LIST

L1 to L14 Approximation curve
1 Metal sheet
3 Conical punch
3a Inclined portion
5 Flat bottomed cylindrical punch
7 Crack

The invention claimed is:

1. A method for manufacturing a press formed part, the method comprising:
   specifying stretch flange limit strain in a metal sheet so as to satisfy formula 1 by using: strain gradient in a radial direction directed from an end portion of the metal sheet at a time a press load is applied; and strain gradient in a sheet thickness direction of the metal sheet that intersects the loading direction; and
   press forming the metal sheet to form the formed part, wherein:

$$\epsilon_{\theta lim}=A[a\cdot\Delta\epsilon_\theta/\Delta r+b\cdot\Delta\epsilon_\theta/\Delta t]+c \qquad \text{formula 1}$$

where $\epsilon_{\theta lim}$ represents the stretch flange limit strain in a tangential direction of a sheet edge,
   $\Delta\epsilon_\theta/\Delta t$ represents the strain gradient in the radial direction,
   $\Delta\epsilon_\theta/\Delta t$ represents the strain gradient in the sheet thickness direction,
   A, a, and b represent influence coefficients, and
   c represents the limit strain at a time the strain gradient is zero.

2. A method for manufacturing a press formed part, the method comprising:
   specifying stretch flange limit strain so as to satisfy formula 2 by using strain gradient in a sheet thickness direction of a metal sheet intersecting a loading direction at a time a press load is applied; and
   press forming the metal sheet to form the formed part, wherein:

$$\epsilon_{\theta lim}=A[b\cdot\Delta\epsilon_\theta/\Delta t]+c \qquad \text{formula 2}$$

where $\epsilon_{\theta lim}$ represents the stretch flange limit strain in a tangential direction of a sheet edge,
   $\Delta\epsilon_\theta/\Delta t$ represents the strain gradient in the sheet thickness direction,
   A and b represent influence coefficients, and
   c represents the limit strain at a time the strain gradient is zero.

3. A method for manufacturing a press formed part, the method comprising:
   acquiring stretch flange limit strain at a sheared edge of a metal sheet by executing a hole expansion test while changing a diameter of an initial hole and a shape of a hole expanding punch;

obtaining strain gradient in a radial direction of the initial hole near the sheared edge after the hole expansion test;

obtaining strain gradient in a sheet thickness direction near the sheared edge after the hole expansion test;

determining feasibility of press forming, which causes stretch flange strain, by using empirical formula 3; and press forming the metal sheet to form the formed part, wherein:

formula 3 represents a relation between stretch flange limit strain $\epsilon_{\theta lim}$ and a value $[a \cdot \Delta\epsilon_\theta/\Delta r + b \cdot \Delta\epsilon_\theta/\Delta t]$ obtained by adding the strain gradient in the radial direction with the strain gradient in the sheet thickness direction, formula 3 is obtained by using: the stretch flange limit strain acquired in the step of acquiring the stretch flange limit strain; the strain gradient in the radial direction obtained in the step of obtaining the strain gradient in the radial direction; and the strain gradient in the sheet thickness direction obtained in the step of obtaining the strain gradient in the sheet thickness direction, $\Delta\epsilon_\theta/\Delta r$ represents the strain gradient in the radial direction, $\Delta\epsilon_\theta/\Delta t$ represents the strain gradient in the sheet thickness direction, and a and b represent influence coefficients.

4. A method for manufacturing a press formed part, the method comprising:

acquiring stretch flange limit strain at a sheared edge of a metal sheet by executing a hole expansion test while changing a diameter of an initial hole and a shape of a hole expanding punch;

obtaining strain gradient in a sheet thickness direction near the sheared edge after the hole expansion test;

determining feasibility of press forming, which causes stretch flange strain, by using empirical formula 4; and press forming the metal sheet to form the formed part, wherein:

formula 4 represents a relation between stretch flange limit strain $\epsilon_{\theta lim}$ and the strain gradient in the sheet thickness direction $[b \cdot \Delta\epsilon_\theta/\Delta t]$, formula 4 is obtained by using: the stretch flange limit strain acquired in the step of acquiring the stretch flange limit strain; and the strain gradient in the sheet thickness direction obtained in the step of obtaining the strain gradient in the sheet thickness direction, $\Delta\epsilon_\theta/\Delta r$ represents the strain gradient in the radial direction, and b represents an influence coefficient.

* * * * *